United States Patent [19]

Kim et al.

[11] Patent Number: 5,520,927
[45] Date of Patent: May 28, 1996

[54] METHOD FOR THE PREPARATION OF SUSTAINED RELEASE SOMATOTROPIN AND PRODUCT PRODUCED THEREBY

[75] Inventors: Nam J. Kim; Byung G. Rhee; Heung S. Cho, all of Daejeon-Si, Rep. of Korea

[73] Assignee: Lucky, Ltd., Seoul, Rep. of Korea

[21] Appl. No.: 275,329

[22] Filed: Jul. 14, 1994

Related U.S. Application Data

[63] Continuation of Ser. No. 944,754, Sep. 14, 1992, abandoned, which is a continuation of Ser. No. 654,025, Feb. 12, 1991, abandoned.

[30] Foreign Application Priority Data

Feb. 12, 1990 [KR] Rep. of Korea ............... 90-1689
Dec. 31, 1990 [KR] Rep. of Korea ............. 90-23104

[51] Int. Cl.⁶ ........................................... A61K 9/127
[52] U.S. Cl. ................................. 424/450; 530/399
[58] Field of Search ......................... 424/450, 400; 530/399

[56] References Cited

U.S. PATENT DOCUMENTS

| 4,861,580 | 8/1989 | Janoff et al. ............ 424/450 |
| 4,985,404 | 1/1991 | Mitchell .................. 514/12 |

FOREIGN PATENT DOCUMENTS

| 193917 | 9/1986 | European Pat. Off. . |
| 246540 | 11/1987 | European Pat. Off. . |
| 314421 | 5/1989 | European Pat. Off. . |
| 87-1825 | 8/1985 | Rep. of Korea . |
| 89-2631 | 7/1989 | Rep. of Korea . |
| 90-6886 | 9/1990 | Rep. of Korea . |

*Primary Examiner*—Thurman K. Page
*Assistant Examiner*—S. Howard
*Attorney, Agent, or Firm*—Birch, Stewart, Kolasch & Birch

[57] ABSTRACT

A parenterally administered, slow releasing bioactive pharmaceutical composition comprises at least one bioactive polypeptide, at least one tocopherol compound, and a release delaying agent.

14 Claims, 11 Drawing Sheets

METHOD FOR THE PREPARATION OF SUSTAINED RELEASE SOMATOTROPIN AND PRODUCT PRODUCED THEREBY

This application is a continuation, of application Ser. No. 07/944,754 filed on Sept. 14, 1992, which is a continuation of application Ser. No. 07/654,025 filed on Feb. 12, 1991, both now abandoned.

BACKGROUND OF THE INVENTION

1. Field of the Invention

The present invention relates to a composition releasing bioactive polypeptides and more particularly, to a parenterally administered, slow releasing bioactive pharmaceutical composition which comprises at least one bioactive polypeptide, at least one tocopherol compound, and a release delaying agent.

2. Description of the Prior Art

Most of bioactive polypeptides have short half-life in vivo. In order to maintain the biological activities of the polypeptides during a desirable duration with sufficient effects when administered, it was necessary to administer an excess amount of bioactive polypeptides or to increase the administration frequency. But, the frequent or excessive administration may injure desired goal. Thus, a means for administering the bioactive polypeptides, capable of prolonging the duration of the biological activities for one administration, have been required.

Recently, various studies for satisfying the requirement have been made. Korean Patent Publication No. 89-2631 discloses that a growth hormone is bound to a transition metal such as Zn and the complex is combined with a gelled oil vehicle comprising a mineral oil or plant oil such as peanut oil or sesame oil, a moisturizing agent and a filler. But, its duration was less than desirable. Furthermore, the growth hormone must be complexed with transition metal. For an example, the complex of a growth hormone and Zn is formed by repeating a series of process comprising adding zinc chloride to a growth hormone under a controlled condition to obtain precipitates with preventing to coagulate the precipitates using sterilized deionized-water and centrifuging, and then lyophilizing. The above method is very tedious and time consuming process.

European Patent No. 246,540 suggests a method that insulin is mixed with fatty acid such as palmitic acid, stearic acid or lauric acid and the mixture is formed to tablets, and then the tablet is transplanted into rats. Korean Patent Publication No. 90-6886 discloses that somatotropin of barrier coating type is transplanted into cows and pigs. However, those methods require a surgical operation or special equipments for the transplantation. And also, the solid substance may give the animal bad feeling in comparison with liquid.

In European Patent No. 193,917, the mixture of a growth hormone with watersoluble or dispersable carbohydrate polymer such as dextran, dextrin, starch, glycogen, cellulose and chitonic acid is administered to cows or pigs and tested. But, the duration was only 7 days. The animal often realized the carbohydrate polymer such as dextran as an antigen and sensitively responsed. Therefore, such a mixture is not suitable as pharmaceutical.

European Patent No. 314,421 discloses a composition combined with an oil (major component), a carbohydrate polymer such as dextran and an assistant. But, the method has same problems as European Patent No. 193,917 does.

Korean Patent Laid Open No. 87-1825 discloses that 40 mg of growth hormone bound to zinc mixed with 8 mg of peanut oil. This formulation is administered to pigs and released for 9 days.

As described above, the known compositions containing bioactive polypeptides over-release or over-expense the active components at initial period after the administration and thus the duration is very short. As well, the compositions may show side-effects occurred by any elements of the composition. Optionally, the polypeptide must be bound to metal such as transition metal.

The present inventors have made studies in order to develop a composition suitable to administer bioactive polypeptides to an animal or human, whose durability is excellent in said body. As a result, we found that a composition combining bioactive polypeptides with tocopherol components and an assistant delaying agent shows the best initial-releasing and the durability in vivo.

Such a composition doesn't give troubles such as side-effects. The composition give a synergic effect, instead. Furthermore, without binding polypeptides to metal, the composition has a sufficient durability. Therefore, said composition will be safer.

SUMMARY OF THE INVENTION

Accordingly, an object of the present invention is to provide a slow releasing bioactive composition including at least one bioactive polypeptide when it is parenterally administered to the animal or human, which comprises at least one bioactive polypeptide, at least one tocopherol selected from the group consisting of tocopherol acetate, tocopherol, and tocopherol and tocopheryl acetate derivatives, and a release delaying agent.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Briefly described, the present invention relates to a parenterally administered, slow releasing bioactive pharmaceutical composition which comprises at least one bioactive polypeptide, at least one tocopherol compound and a release delaying agent.

BRIEF DESCRIPTION OF THE DRAWINGS

The present invention will become more fully understood from the detailed description given hereinbelow and the accompanying drawings which are given by way of illustration only, and thus are not limiting of the present invention, and wherein.

DESCRIPTION OF THE PREFERRED EMBODIMENTS

Figure 1:
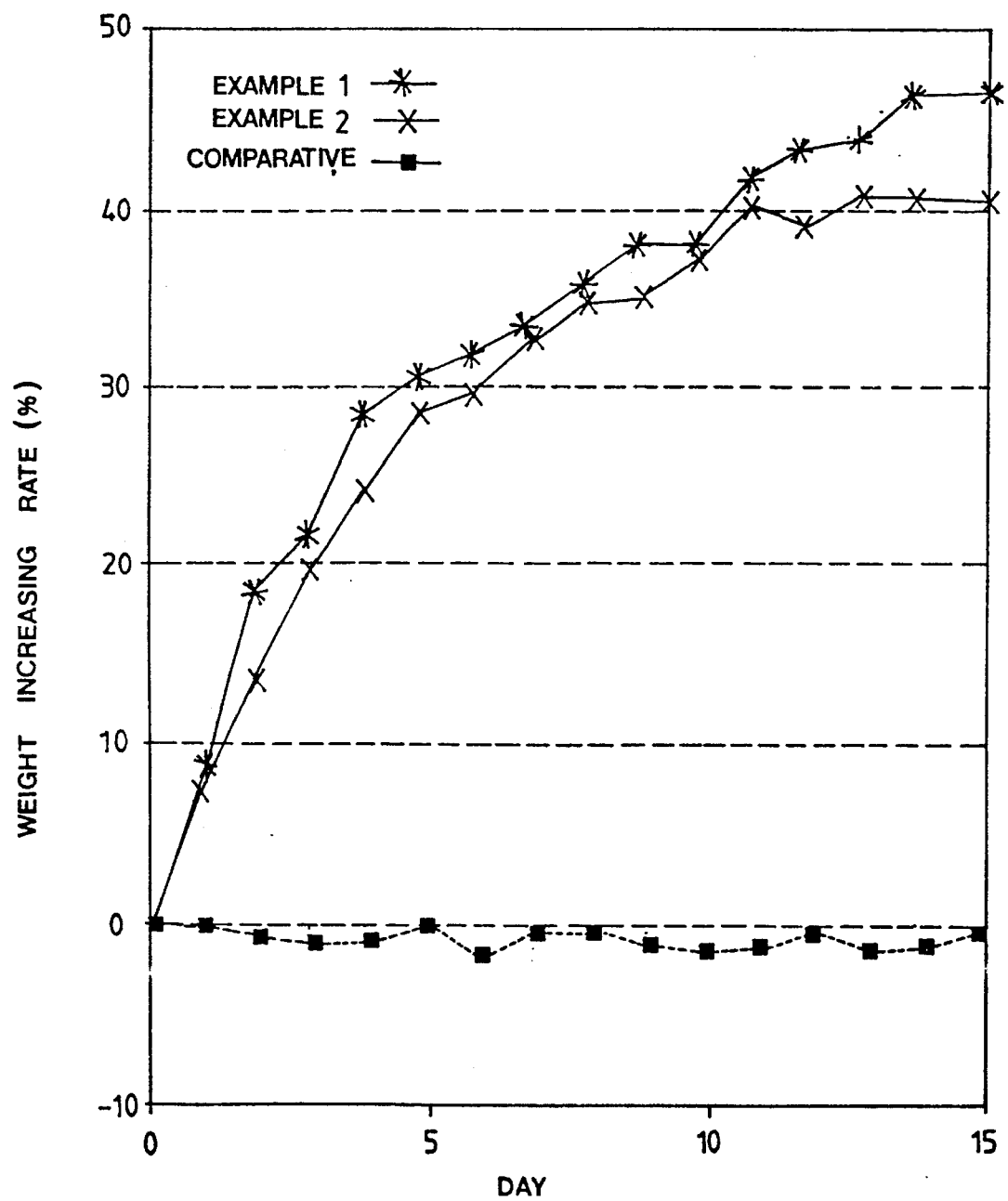
FIGS. 1–6 are graphs showing the effects on the body weight when the composition of the present invention is injected.
Figure 2:
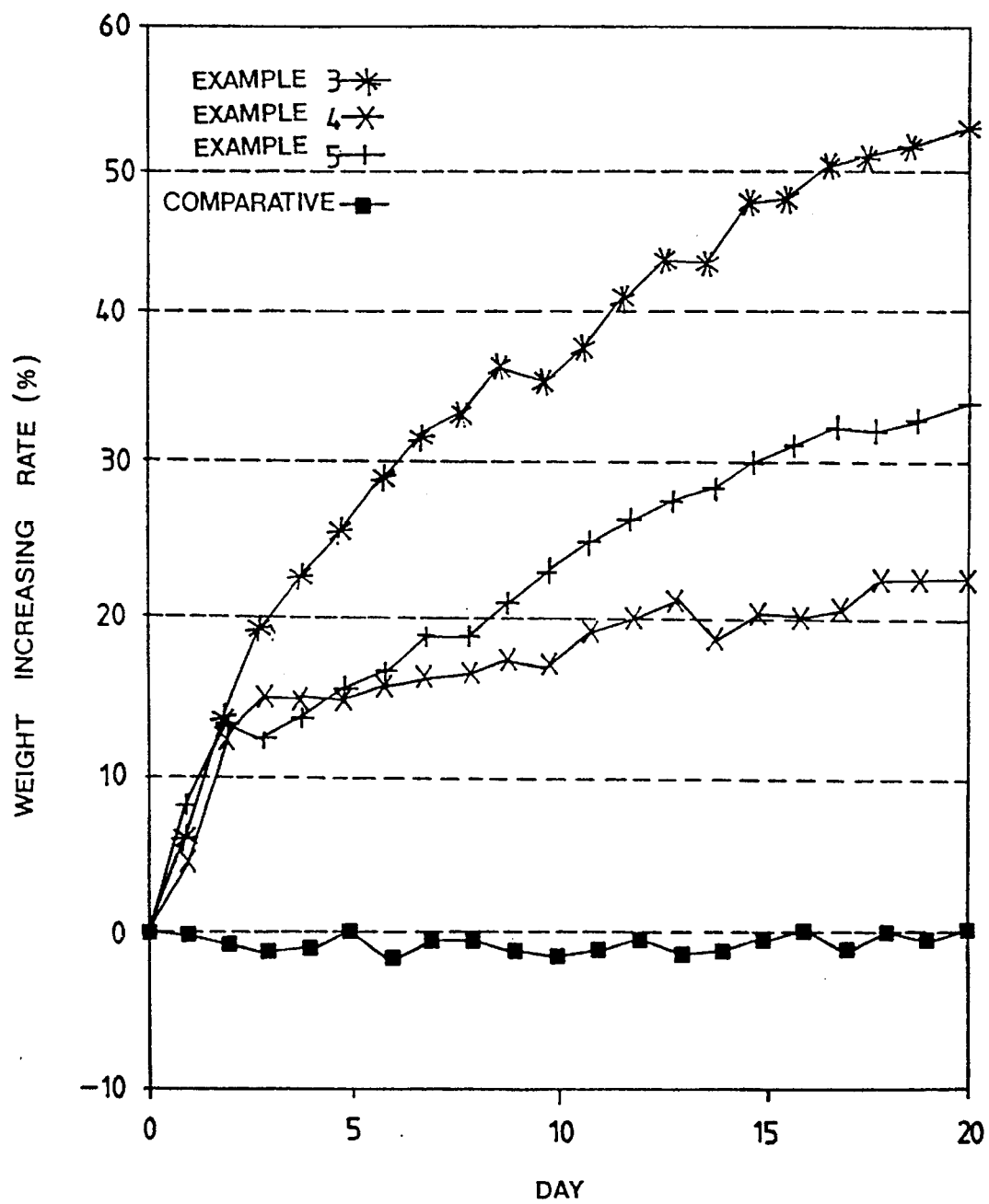
Figure 3:
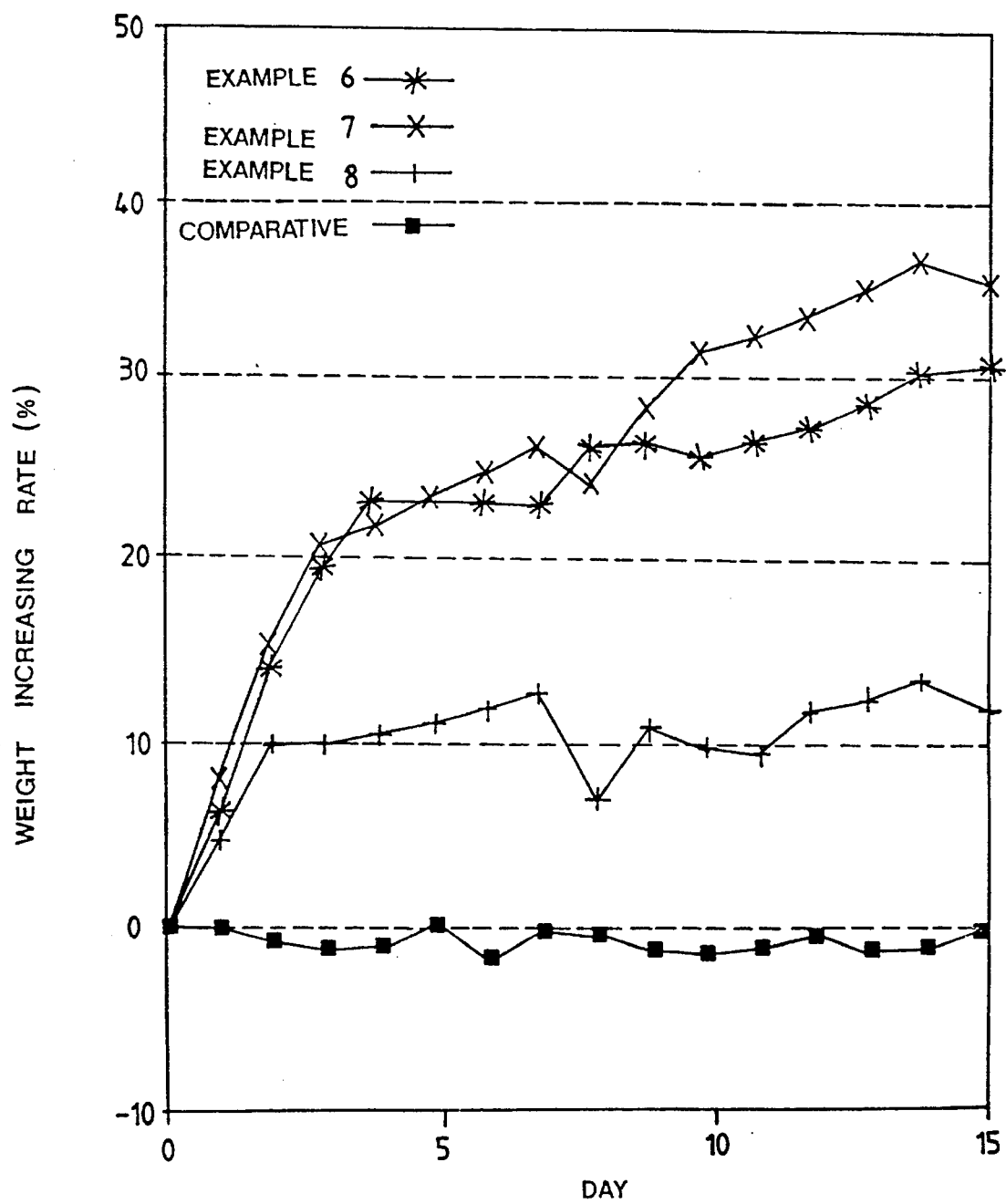
Figure 4:
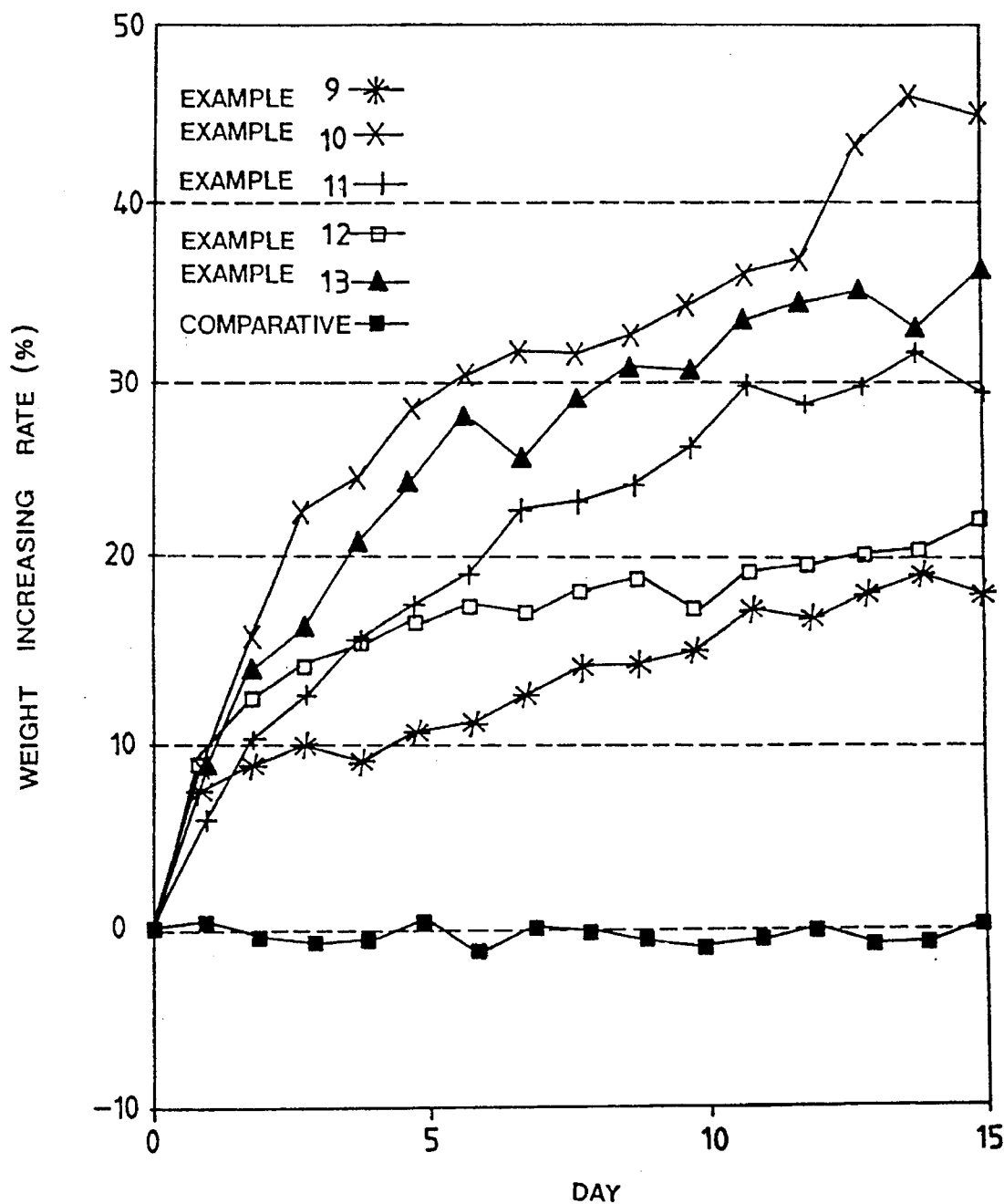
Figure 5:
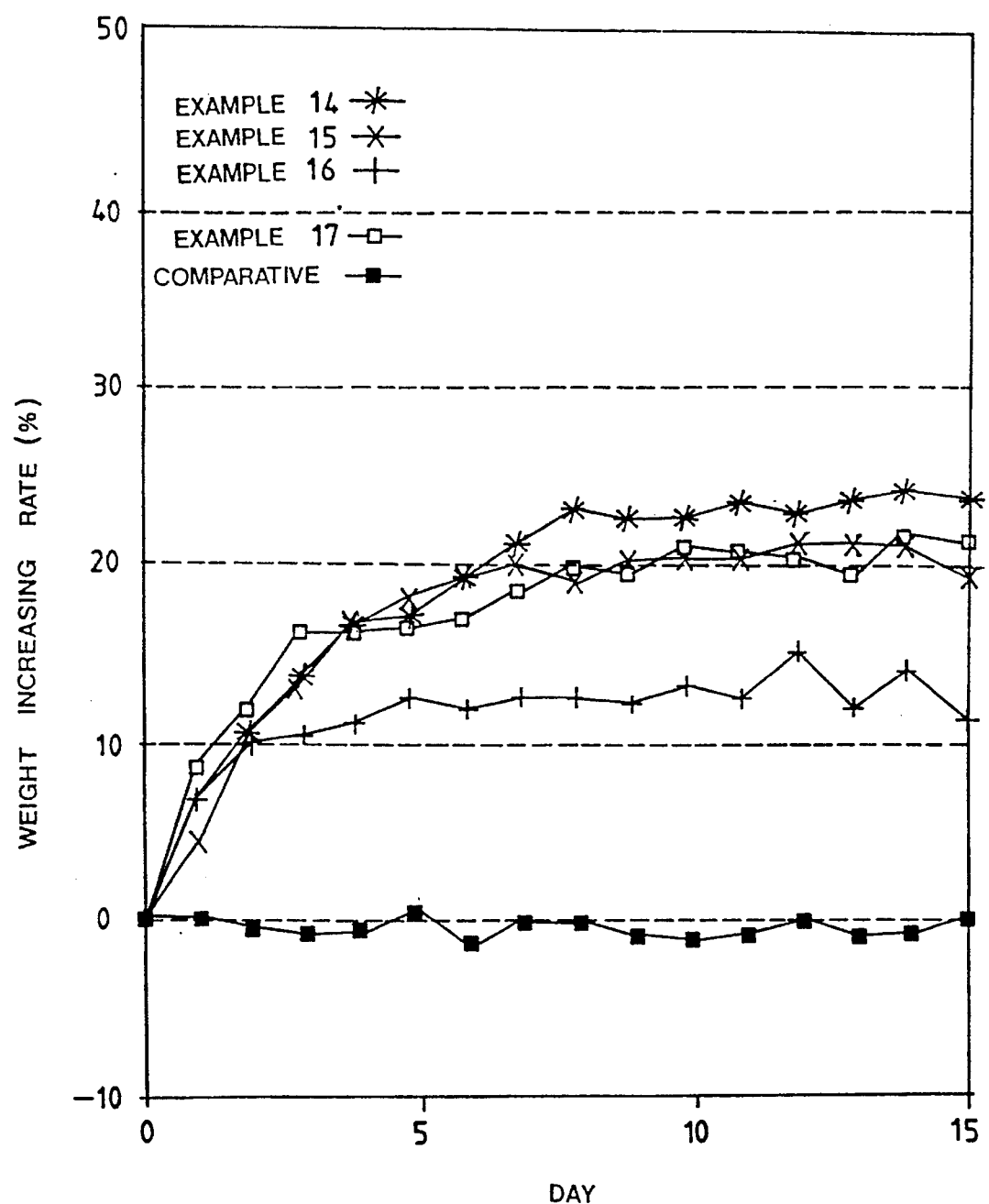
Figure 6:
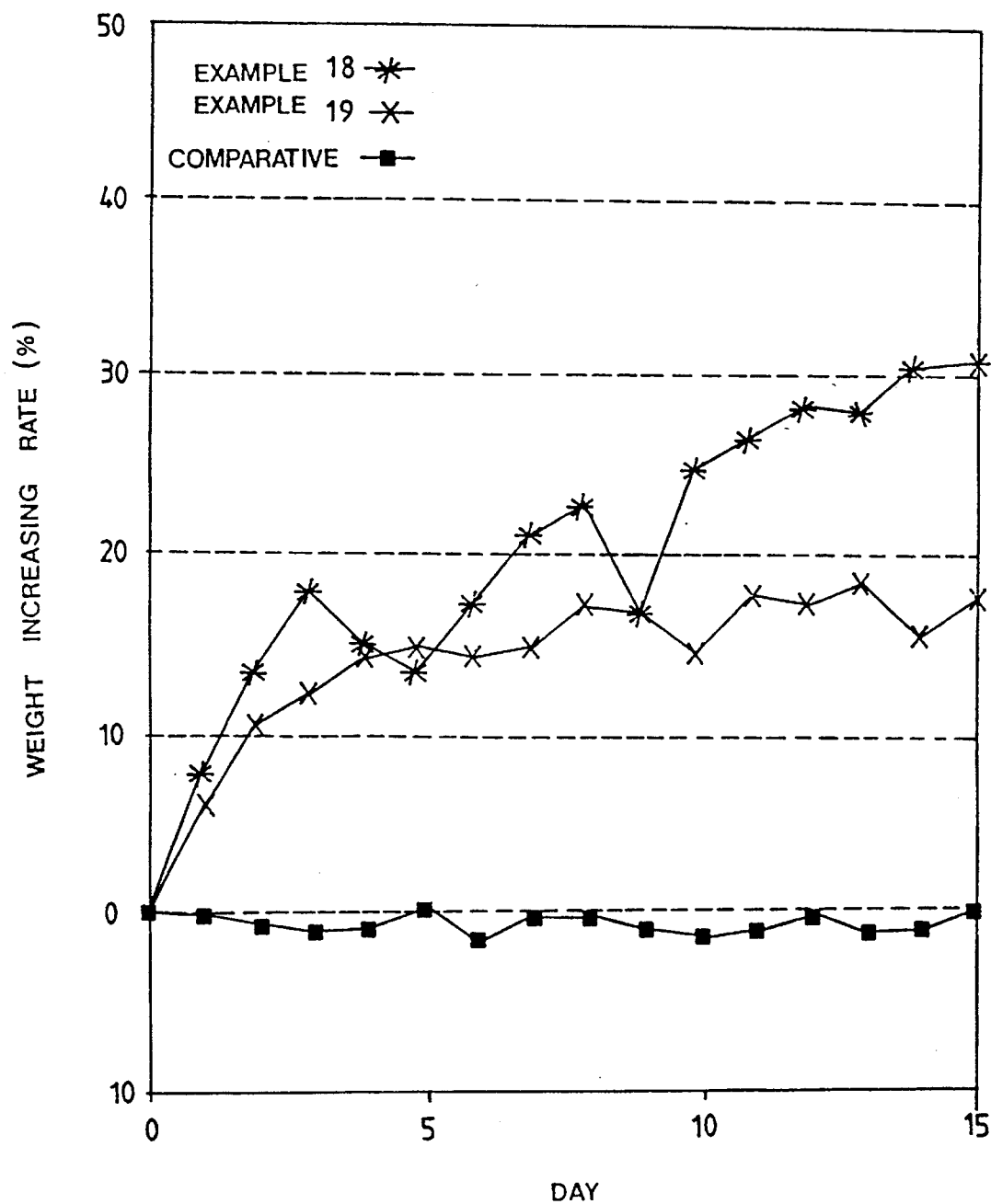

Referring now in detail to the drawings for the purpose of illustration and the preferred embodiments of the present invention, the slowly releasing composition of bioactive polypeptides as shown in FIGS. 1 to 14, comprises at least one bioactive polypeptide, at least one tocopherol compound, and a lecithin. The tocopherol compound is selected from the group consisting of tocopherol, tocopherol acetate, tocopherol derivatives, and tocopheryl acetate derivative.

The bioactive polypeptide according to the present invention includes all the known bioactive polypeptides, for examples, growth hormones, insulin, interferon, interleukin II, tumor necrosis factor, colony stimulating factor and derivatives thereof.

Of the bioactive polypeptides, somatotropin is very suitable for the present invention due to its short half-life thereof in vivo. Examples for somatotropins include animal somatotropins such as bovine somatotropin, porcine somatotropin, goat or sheep somatotropin, salmon growth hormone, eel growth hormone and human growth hormone.

The somatotropin can be obtained from a pituitary gland of animal. Alternatively, the somatotropin may be obtained by recombinant DNA-technology.

The polypeptide may be used in the form bound or unbound to metal in the present invention. However, the bound form is not necessary, because the composition has the sufficient durability although the polypeptide is not bound with metal or any materials conventionally used for decreasing the solubility of the polypeptide in an aqueous solution in this field.

Tocopheryl acetate, tocopherol, and derivatives thereof used in the composition of the present invention have pharmacological activities as well as its function in delaying the release of the polypeptides. For examples, tocopherol compound helps the normal reproduction in a rat, a mouse, a guinea pig, a pig, or fowls, prevent the defects of muscle development in a young sheep, a calf or a dog, prevent softening of brain, irregulation of muscle movement, hardening of muscle, underexercise and tetanus in a chicken, and prevent steatitis in a mink, a pig, or a cat.

The composition of the present invention contains an assistant release delaying agent as well as tocopherol compound for the purpose of more excellent durability. Various assistant delaying agents are known. Particularly, choline derivatives, aluminum monostearate, calcium stearate, wax, carnauba wax, and paraffine are preferable to other known assistant delaying agents. As an assistant delaying agent of the present invention, one or more compounds selected from a group consisting of compounds listed above are used.

Especially, choline derivatives are preferred. Examples of choline derivatives include phosphatidyl choline, lysophospholipid, plasmalogen, sphingomyelin etc. Phosphatidyl choline can be extracted from soybean, bovine liver, bovine heart or egg yolk.

The amount of the bioactive polypeptides used in the composition is wide. The lower limit is a minimum amount of polypeptide required to exert its effect in the body. The upper limit is a maximum amount of polypeptide capable of being contained in the tocopherol component used. Without any special purpose, it is not necessary to use the polypeptide in an excess amount.

When the total of the tocopherol component and the assistant delaying agent is 100% by weight, the assistant delaying agent is conventionally 2 to 10% by weight, preferably 2 to 7% by weight, more preferably 2 to 5% by weight, and the tocopherol component is the rest.

The composition of the present invention may be prepared by mixing at least one tocopherol component and an assistant delaying agent and then combining at least one bioactive polypeptide thereto. Alternative method comprises dispersing at least one bioactive polypeptide in an assistant delaying agent and then combining the dispersion with tocopherol component. The tocopherol component and an assistant delaying agent are added to a beaker.

The beaker is placed in an oil bath at a temperature between about 130° C. and 160° C., preferably 140° C. and 150° C, for about 10 to 40 minutes, preferably 20 to 30 minutes.

In prior arts, the polypeptide must be used in the form bound to metal or transition metal to decrease the solubility and it is used in an excess amount to make up for the loss resulted from the initial burst effect. But, the composition of the present invention has an excellent durability without any binding of the polypeptide to the metal. The present invention has no problems such as side-effects occurred from metal bound to the polypeptide. The tocopherol component used in the present invention has a pharmacological functions such as the preventation or alleviation of the sensitive response against foreign materials in vivo. Furthermore, according to the present invention, the initial releasing of the effective component is reasonable and the bioavailability is increased. Both of the preparation and the administration of the composition become simple and convenient.

The present invention will now be described in more detail in connection with the following examples which should be considered as being exemplary and not limiting the present invention.

Example 1

500 ml of bovine somatotropin (18 mg/ml produced by Lucky Ltd.) and 3 g of L-α-phosphatidyl choline (L-α-lecithin) extracted from soybeans were mixed in a homomixer for 10 minutes and operated in a microfluidizer at 40° C. for 5 minutes. This emulsion was put into a bottle, rapidly cooled to −70° C. using dry ice and acetone and then lyophilized.

The lyophilized mixture was ground and 161.8 mg (bovine somatotropin content 100 mg) was suspended in 1 ml of tocopheryl acetate. The mixture was homogenized in a homomixer for 5 minutes.

Thus obtained somatotropin compositions were injected to animals and tested for the effect on the body weight.

The test was carried out using female SD rats weighing about 80 to 100 g. The rats were subjected to a peripharyngeal method to eliminate their pituitaries. After 2 weeks, their body weights were measured at regular time everyday for 1 week. The rats whose body weights were not changed were selected, and subjected to as follows;

Bovine somatotropin compositions were injected to three hypophysectomized rats subcutaneously into their abdominal region by an amount of 0.1 ml per head. As a control group, only tocopheryl acetate was injected. Their body weights were measured at regular time everyday, the increase rate of the body weight to one before injection was calculated. The results are shown in Table 1 and FIG. 1.

Example 2

The composition was prepared according to the same procedure as in Example 1, except that L-α-phosphatidyl choline was not passed through a microfluidizer. The compositions were tested by the same method as Example 1 and the results are shown in Table I and FIG. 1.

TABLE 1

The rate of body weight affected from the injection of the bovine somatotropin compositions, %

| Day | Example 1 | Example 2 | Control |
|---|---|---|---|
| 1 | 8.1 | 7.5 | −0.2 |
| 2 | 18.4 | 13.5 | −0.8 |
| 3 | 21.4 | 19.8 | −1.2 |
| 4 | 28.2 | 24.2 | −1.0 |
| 5 | 30.3 | 28.6 | 0.0 |
| 6 | 31.5 | 29.5 | −1.6 |
| 7 | 33.4 | 32.6 | −0.4 |
| 8 | 35.8 | 34.9 | −0.5 |
| 9 | 38.0 | 35.1 | −1.2 |
| 10 | 38.0 | 37.3 | −1.5 |
| 11 | 41.9 | 40.3 | −1.2 |
| 12 | 43.6 | 39.1 | −0.5 |
| 13 | 44.3 | 40.8 | −1.3 |
| 14 | 47.2 | 40.7 | −1.2 |
| 15 | 47.2 | 40.5 | −0.3 |

Example 3

The composition was prepared according to the same procedure as in Example 1, except that 200 ml of porcine somatotropin (24 mg/ml) and 1.58 g of L-α-phosphatidyl choline were used. Thus obtained compositions were tested by the same method as Example 1 and the results are shown in Table 2 and FIG. 2.

Example 4

The composition was prepared according to the same procedure as Example 3, except that 0.5 ml of tocopherol acetate and 0.5 ml of sesame oil were used. The compositions were tested by the same method as Example 1 and the results are shown in Table 2 and FIG. 2.

Example 5

The composition was prepared according to the same procedure as Example 4, except that peanut oil instead of sesame oil was used. The compositions were tested by the same method as Example 1 and the results are shown in Table 2 and FIG. 2.

TABLE 2

The increase rate of body weight affected from the injection of the porcine somatotropin compositions, %

| Day | Example 3 | Example 4 | Example 5 | Control |
|---|---|---|---|---|
| 1 | 6.6 | 4.6 | 8.1 | −0.2 |
| 2 | 13.6 | 2.5 | 13.4 | −0.8 |
| 3 | 19.7 | 15.0 | 12.4 | −1.2 |
| 4 | 22.6 | 14.3 | 13.9 | −1.0 |
| 5 | 25.5 | 14.9 | 15.4 | 0.0 |
| 6 | 29.0 | 15.7 | 16.4 | −1.6 |
| 7 | 31.8 | 16.1 | 18.9 | −0.4 |
| 8 | 33.5 | 16.3 | 18.7 | −0.5 |
| 9 | 36.3 | 17.5 | 21.1 | −1.2 |
| 10 | 35.2 | 17.02 | 3.0 | −1.5 |
| 11 | 37.6 | 19.2 | 25.2 | −1.2 |
| 12 | 41.1 | 19.9 | 26.4 | −0.5 |
| 13 | 43.7 | 21.2 | 27.5 | −1.3 |
| 14 | 43.5 | 18.5 | 28.2 | 1.2 |
| 15 | 47.7 | 20.4 | 30.2 | 0.3 |
| 16 | 48.3 | 20.0 | 31.4 | 0.0 |
| 17 | 50.3 | 20.5 | 32.6 | −1.2 |
| 18 | 50.9 | 22.6 | 32.4 | −0.1 |
| 19 | 51.8 | 22.6 | 33.0 | −0.4 |
| 20 | 53.0 | 22.7 | 34.0 | 0.0 |

Example 6

The composition was prepared according to the same procedure as Example 1, except that 1 ml of tocopheryl acetate and 33 mg of L-α-phosphatidyl choline were mixed in a homomixer and hereto the 100 mg of lyophilized porcine somatotropin was added. The compositions were tested by the same method as Example 1 and the results are shown in Table 3 and FIG. 3.

Example 7

The composition was prepared according to the same procedure as Example 3, except that 2 ml of tocopheryl acetate was used. The compositions were tested by the same method as Example 1 and the results are shown in Table 3 and FIG. 3.

Example 8

The composition was prepared according to the same procedure as Example 3, except that peanut oil instead of tocopheryl acetate was used. The compositions were tested by the same method as Example 1 and the results are shown in Table 3 and FIG. 3.

TABLE 3

The increase rate of body weight affected from the injection of the porcine somatotropin compositions, %

| Day | Example 6 | Example 7 | Example 8 | Control |
|---|---|---|---|---|
| 1 | 6.2 | 8.0 | 4.7 | −0.2 |
| 2 | 14.1 | 14.8 | 10.1 | −0.8 |
| 3 | 19.7 | 20.7 | 10.0 | −1.2 |
| 4 | 23.4 | 22.1 | 10.4 | −1.0 |
| 5 | 23.3 | 23.3 | 11.1 | 0.0 |
| 6 | 23.4 | 24.9 | 11.9 | −1.6 |
| 7 | 23.1 | 26.2 | 12.9 | −0.4 |
| 8 | 26.3 | 24.3 | 6.9 | −0.5 |
| 9 | 26.6 | 28.3 | 10.8 | −1.2 |
| 10 | 25.9 | 31.5 | 9.9 | −1.5 |
| 11 | 26.7 | 32.3 | 9.6 | −1.2 |

TABLE 3-continued

The increase rate of body weight affected from the injection of the porcine somatotropin compositions, %

| Day | Example 6 | Example 7 | Example 8 | Control |
|-----|-----------|-----------|-----------|---------|
| 12  | 27.2      | 33.5      | 11.8      | −0.5    |
| 13  | 28.7      | 35.2      | 12.5      | −1.3    |
| 14  | 30.5      | 37.1      | 13.7      | −1.2    |
| 15  | 30.4      | 35.6      | 12.1      | −0.3    |

Example 9

The composition was prepared according to the same procedure as Example 1, except that 400 ml of bovine somatotropin (23 mg/ml) and 3.102 g of L-α-phosphatidyl choline were mixed. 13.3 mg of lyophilized mixture bovine somatotropin content 10 mg was added to 1 ml of tocopherol acetate. The compositions were tested by the same method as Example 1 and the results are shown in Table 4 and FIG. 4.

Example 10

The composition was prepared according to the same procedure as Example 9, except that 66.5 mg of lyophilized mixture (bovine somatotropin content 50 mg) was added to 1 ml of tocopheryl acetate. The compositions were tested by the same method as Example 1 and the results are shown in Table 4 and FIG. 4.

Example 11

The composition was prepared according to the same procedure as Example 1, except that 100 mg of lyophilized bovine somatotropin without L-α-phosphatidyl choline was mixed with 1 ml of tocopheryl acetate. The compositions were tested by the same method as Example 1 and the results are shown in Table 4 and FIG. 4.

Example 12

Example 1, except that 1 ml of tocopherol acetate and 20 mg of aluminum monostearate were heated to 150° C. for 5 minutes and then cooled to room temperature 100 mg of bovine somatotropin without L-α-phosphatidyl choline was suspended in this mixture. The compositions were tested by the same method as Example 1 and the results are shown in Table 4 and FIG. 4.

Example 13

The composition was prepared according to the same procedure as Example 12, except that bovine somatotropin bound to Zn was used. The compositions were tested by the same method as Example 1 and the results are shown in Table 4 and FIG. 4.

TABLE 4

The increase rate of body weight affected from the injection of the bovine somatotropin composition, %

| Day | Example 9 | Example 10 | Example 11 | Example 12 | Example 13 | Control |
|-----|-----------|------------|------------|------------|------------|---------|
| 1   | 8.7       | 8.8        | 7.3        | 7.9        | 5.5        | −0.2    |
| 2   | 12.2      | 13.9       | 8.8        | 15.5       | 9.9        | −0.8    |
| 3   | 13.9      | 16.1       | 9.6        | 22.4       | 12.4       | −1.2    |
| 4   | 15.2      | 20.9       | 8.9        | 24.0       | 15.5       | −1.0    |
| 5   | 16.3      | 24.2       | 10.5       | 28.0       | 17.2       | 0.0     |
| 6   | 17.2      | 27.8       | 10.8       | 30.0       | 19.0       | −1.6    |
| 7   | 16.9      | 25.5       | 12.6       | 31.7       | 22.5       | −0.4    |
| 8   | 18.1      | 29.0       | 14.1       | 31.3       | 22.8       | −0.5    |
| 9   | 18.9      | 30.6       | 14.1       | 32.2       | 23.8       | −1.2    |
| 10  | 17.1      | 30.2       | 14.8       | 34.1       | 25.9       | −1.5    |
| 11  | 19.2      | 33.5       | 17.2       | 36.1       | 29.3       | −1.2    |
| 12  | 19.6      | 34.4       | 16.4       | 36.7       | 28.2       | −0.5    |
| 13  | 20.2      | 35.2       | 18.2       | 43.6       | 29.4       | −1.3    |
| 14  | 20.4      | 32.9       | 19.2       | 46.5       | 31.3       | −1.2    |
| 15  | 21.9      | 36.1       | 18.1       | 45.4       | 29.1       | −0.3    |

Example 14

The composition was prepared according to the same procedure as Example 1, except that 1 ml of tocopheryl acetate and 20 mg of polyethylene glycol-75 lanolin (PEG-75 Lanolin or Solan E) were mixed in a homomixer and hereto 100 mg of bovine somatotropin bound to Zn was added. The compositions were tested by the same method as in Example 1 and the results are shown in Table 5 and FIG. 5.

Example 15

The composition was prepared according to the same procedure as Example 14, except that 1 ml of tocopherol acetate and 33 mg of ARLACEL 165 (a complex of glyceryl monastearate and PEG-100 stearate) instead of PEG-75 lanolin was used. The compositions were tested by the same method as Example 1 and the results are shown in Table 5 and FIG. 5.

Example 16

The composition was prepared according to the same procedure as Example 12, except that the spray-dried bovine somatotropin instead of the lyophilized bovine somatotropin was used. The compositions were tested by the same method as Example 1 and the results are shown in Table 5 and FIG. 5.

Example 17

The composition was prepared according to the same procedure as Example 12, except that 10 mg of aluminum monostearate and 10 mg of cholesterol were used. The compositions were tested by the same method as Example 1 and the results are shown in Table 5 and FIG. 5.

TABLE 5

The increase rate of body weight affected from the injection of the bovine somatotropin compositions, %

| Day | Example 14 | Example 15 | Example 16 | Example 17 | Control |
|-----|------------|------------|------------|------------|---------|
| 1   | 6.9        | 4.1        | 8.5        | 6.7        | −0.2    |
| 2   | 10.9       | 10.3       | 11.7       | 9.9        | −0.8    |
| 3   | 13.7       | 13.3       | 16.1       | 10.2       | −1.2    |
| 4   | 16.7       | 16.6       | 16.1       | 11.0       | −1.0    |
| 5   | 17.2       | 18.1       | 16.3       | 12.5       | 0.0     |
| 6   | 19.2       | 19.6       | 16.9       | 11.8       | −1.6    |

TABLE 5-continued

The increase rate of body weight affected from the injection of the bovine somatotropin compositions, %

| Day | Example 14 | Example 15 | Example 16 | Example 17 | Control |
|---|---|---|---|---|---|
| 7  | 21.6 | 20.3 | 18.7 | 12.5 | −0.4 |
| 8  | 23.4 | 19.1 | 20.0 | 12.5 | −0.5 |
| 9  | 22.6 | 20.4 | 19.6 | 12.3 | −1.2 |
| 10 | 22.8 | 20.5 | 21.2 | 13.2 | −1.5 |
| 11 | 23.9 | 20.6 | 21.0 | 12.4 | −1.2 |
| 12 | 23.1 | 21.6 | 20.6 | 15.1 | −0.5 |
| 13 | 23.9 | 21.5 | 19.9 | 11.9 | −1.3 |
| 14 | 24.6 | 21.6 | 22.0 | 14.1 | −1.2 |
| 15 | 24.0 | 19.8 | 21.9 | 11.3 | −0.3 |

Example 18

The composition was prepared according to the same procedure as Example 12, except that Zn-bound bovine somatotropin was used. The compositions were tested by the same method as Example 1 and the results are shown in Table 6 and FIG. 6.

Example 19

The composition was prepared according to the same procedure as Example 12, except that Zn-bound porcine somatotropin instead of bovine somatotropin was used. The compositions were tested by the same method as Example 1 and the results are shown in Table 6 and FIG. 6.

TABLE 6

The increase rate of body weight affected from the injection of the bovine somatotropin compositions, %

| Day | Example 18 | Example 19 | Control |
|---|---|---|---|
| 1  | 8.0  | 5.9  | −0.2 |
| 2  | 13.6 | 10.4 | −0.8 |
| 3  | 17.9 | 12.3 | −1.2 |
| 4  | 14.8 | 14.4 | −1.0 |
| 5  | 13.5 | 14.7 | 0.0 |
| 6  | 17.3 | 14.1 | −1.6 |
| 7  | 21.0 | 14.6 | −0.4 |
| 8  | 22.8 | 17.3 | −0.5 |
| 9  | 16.7 | 16.9 | −1.2 |
| 10 | 24.6 | 14.3 | −1.5 |
| 11 | 26.4 | 17.6 | −1.2 |
| 12 | 28.2 | 17.1 | −0.5 |
| 13 | 27.9 | 18.4 | −1.3 |
| 14 | 30.3 | 15.3 | −1.2 |
| 15 | 30.5 | 17.5 | −0.3 |

Example 20

30 ml of tocopherol acetate and 600 mg of aluminum monostearate were put into a 50 ml-beaker. Separately, a beaker containing 150 ml of tocopheryl acetate was heated at 150° C. on a temperature-controlled hot plate stirrer. The content of the former beaker was added to the latter and the mixture was heated in an oil bath with stirring bar for 20 minutes to dissolve aluminum monostearate. The mixture was removed from the bath, kept under vacuum and allowed to cool to 25° C. On cooling, the solution converted to a thick gel. 3 g of bovine somatotropin produced by Lucky LTD. was added to the gel and heated to 40° C. After stirring for 2 hours, 10 ml of composition was filled in a 20 ml-syringe having a 15 gauge needle.

The compositions were injected into two Holstein cows in the second trimester of their second lactation. The compositions were injected subcutaneously in the suprascapular region. Two cows were used as a control group without any injection. The daily milk production was accumulated. The increase ratio of the increase rate in an injected group to one in a control group was calculated as following;

$$\text{increase ratio (\%)} = \frac{\text{the increase rate of the milk production in an injected group}}{\text{the increase rate of the milk production in a control group}} \times 100$$

Figure 7:
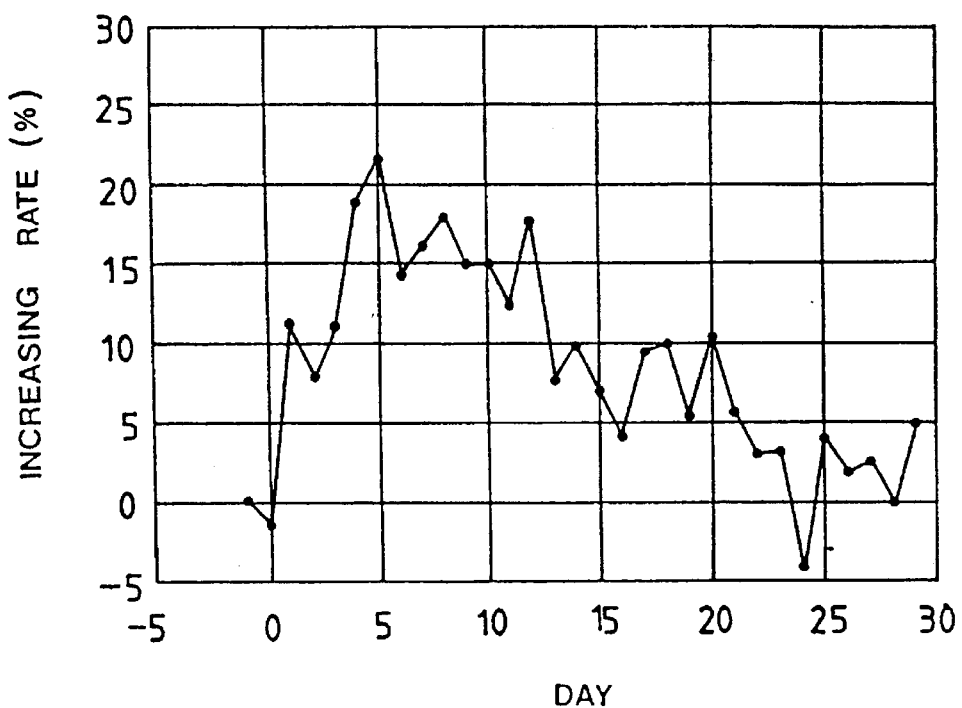
FIG. 7 is a graph showing the effect on the milk production when the composition of the present invention is injected.
Figure 8:
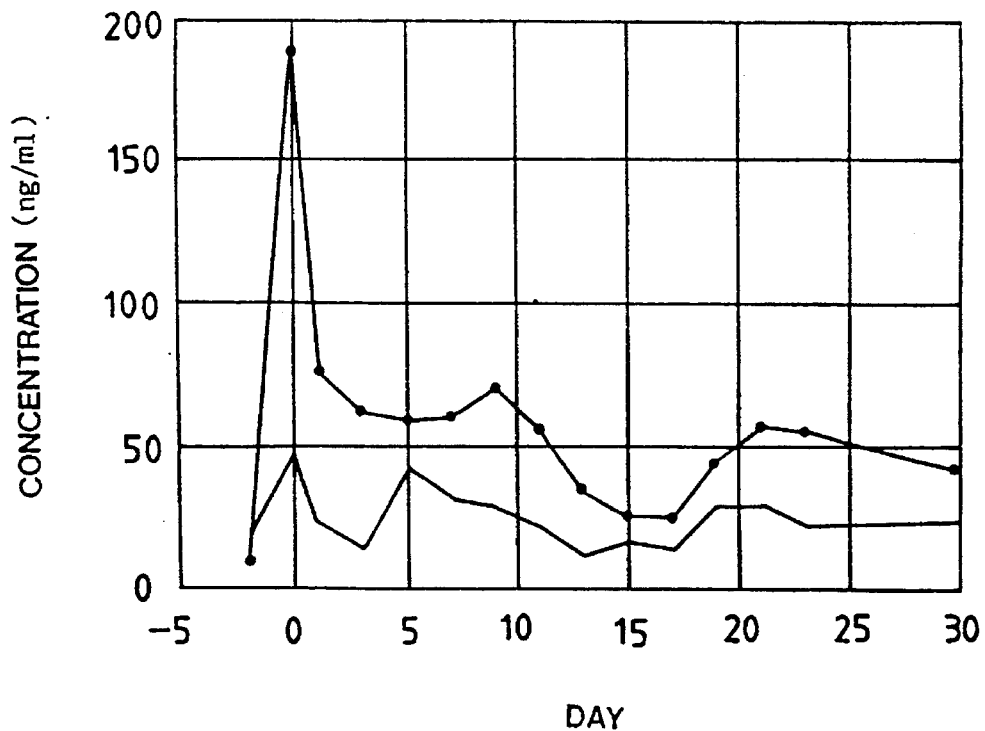
FIG. 8 is a graph showing the polypeptide concentration in serum when the composition of the present invention is injected.
Figure 9:
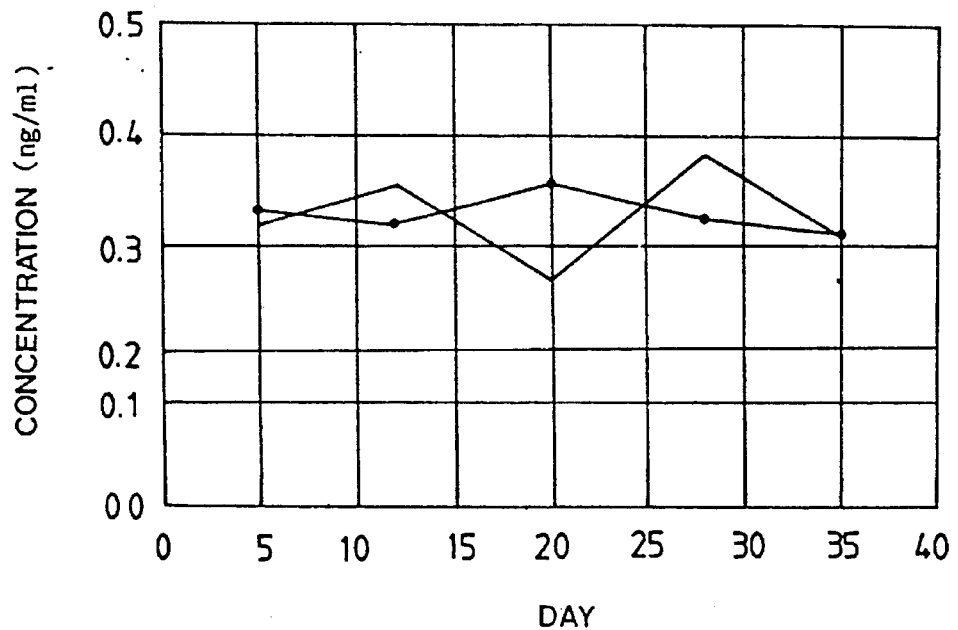
FIG. 9 is a graph showing the polypeptide concentration in milk when the composition of the present invention is injected.
Figure 10:
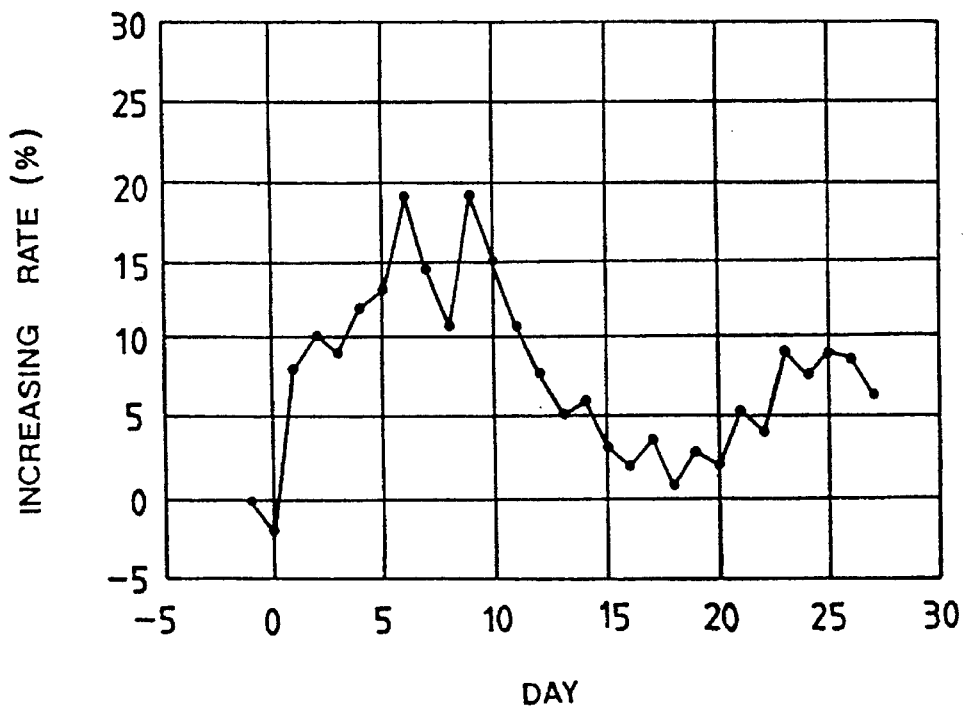
FIG. 10 is a graph showing the effect on the milk production when the composition of the present invention is injected.
Figure 11:
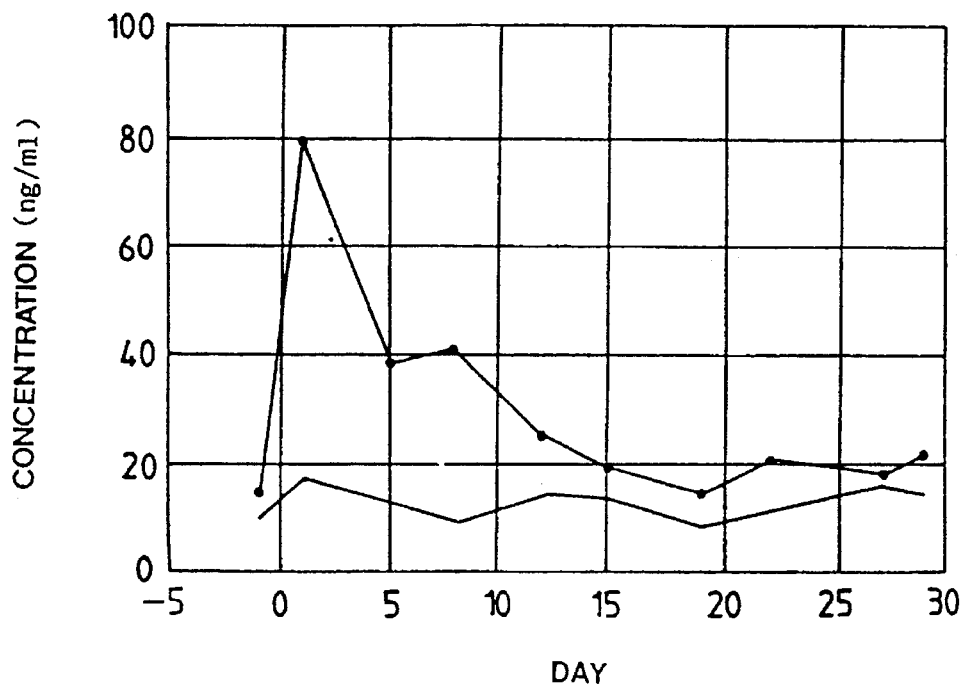
FIG. 11 is a graph showing the polypeptide concentration in serum when the composition of the present invention is injected.
Figure 12:
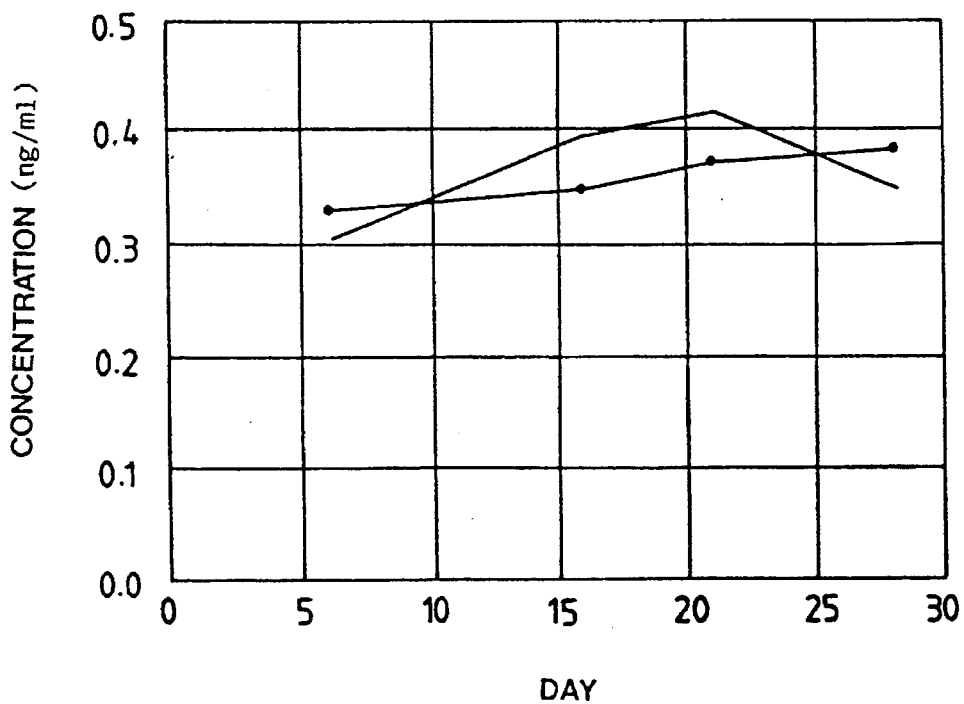
FIG. 12 is a graph showing the polypeptide concentration in milk when the composition of the present invention is injected.
Figure 13:
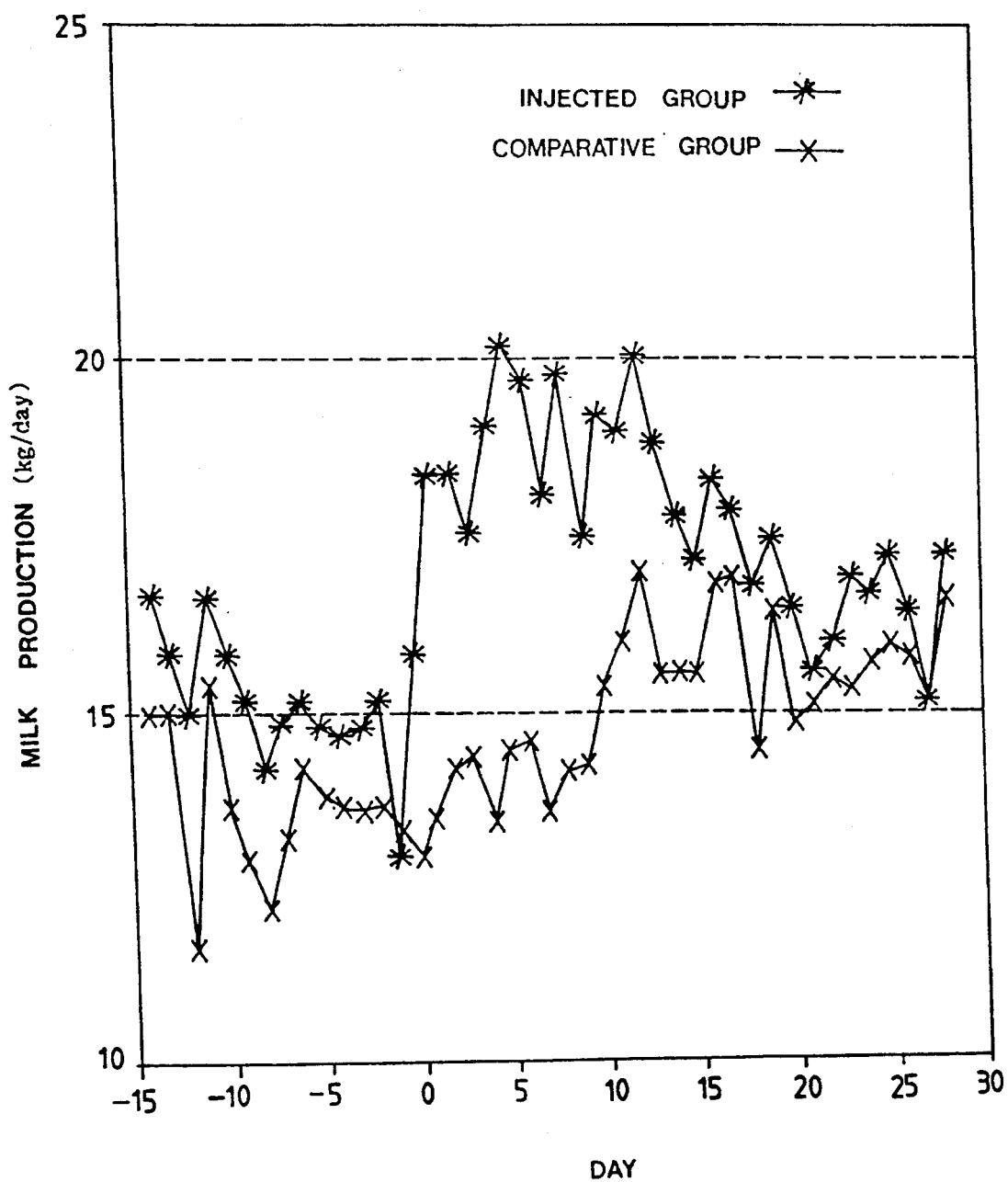
FIG. 13 is a graph showing the effect on the milk production when the composition of the present invention is injected.
Figure 14:
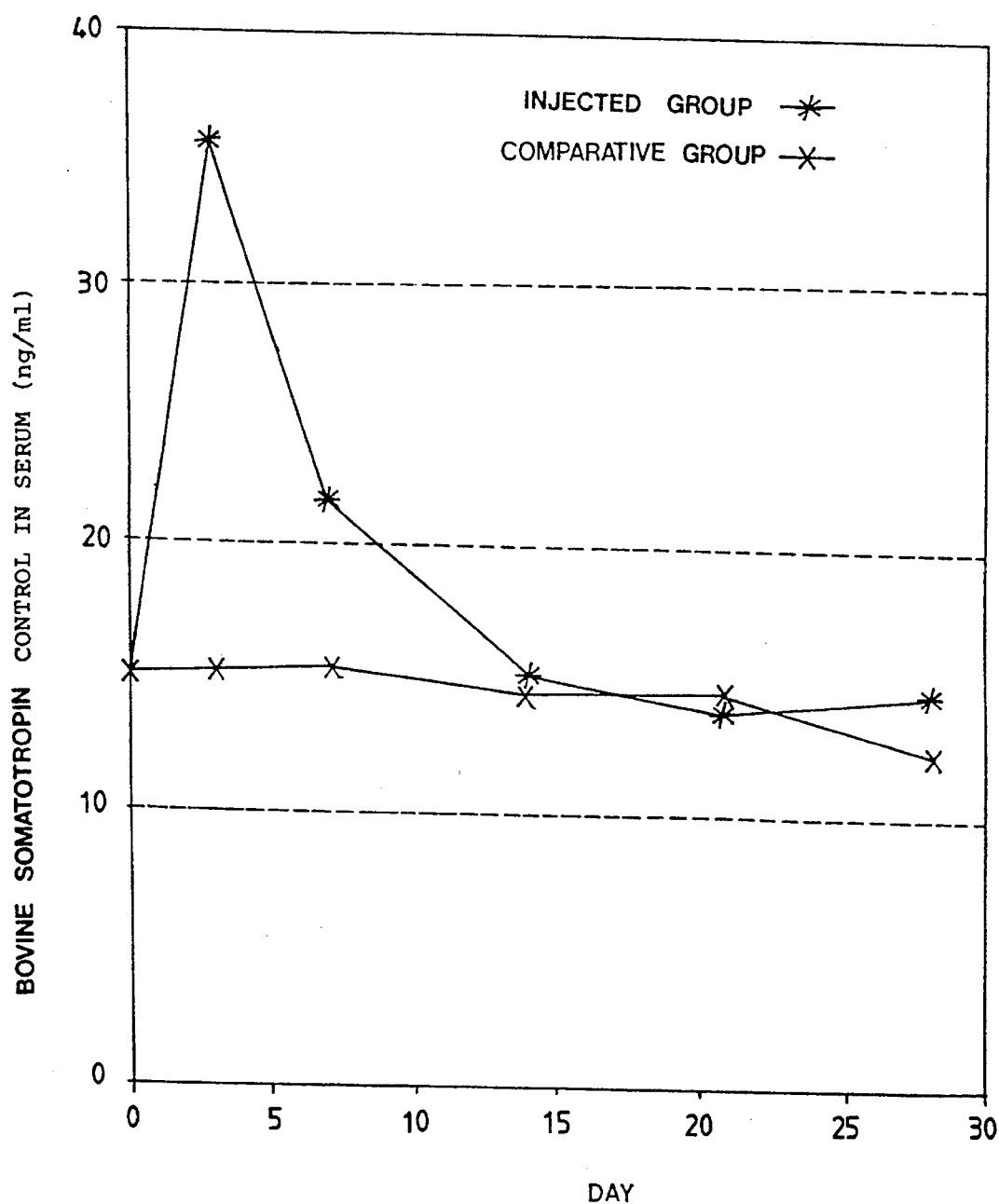
FIG. 14 is a graph showing the polypeptide concentration in serum when the composition of the present invention is injected.

The results are shown in Table 7 and FIG. 7.

TABLE 7

Cumulative average daily milk production, kg/day

| Day | Injected group | Control group | Increase ratio (%) |
|---|---|---|---|
| −5−0 | 24.5 | 27.9− | — |
| −7   | 27.6 | 27.5 | 14.3 |
| −14  | 27.8 | 27.7 | 13.9 |
| −21  | 27.3 | 27.8 | 11.7 |
| −30  | 26.6 | 27.8 | 8.7  |

Blood samples were analyzed for bovine somatotropin. Representative analyses by radioimmunoassay are shown in Table 8 and FIG. 8 where the concentrations of bovine somatotropin in blood serum are expressed in nanograms per milliliter.

TABLE 8

The average concentration of bovine somatotropin in serum, ng/ml

| Day | Injected group | Control group |
|---|---|---|
| −2 | 9.2   | 16.9 |
| 0  | 187.7 | 48.2 |
| 1  | 75.1  | 22.7 |
| 3  | 61.3  | 13.3 |
| 5  | 58.4  | 41.3 |
| 7  | 60.0  | 31.3 |
| 9  | 69.3  | 28.6 |
| 11 | 54.9  | 21.1 |
| 13 | 33.4  | 11.3 |
| 15 | 24.9  | 16.0 |
| 17 | 24.4  | 13.3 |
| 19 | 43.5  | 28.9 |
| 21 | 55.7  | 29.3 |
| 23 | 54.2  | 22.2 |
| 30 | 54.2  | 23.7 |

Milk samples were analyzed for bovine somatotropin. Representative analyses by radioimmunoassay are shown in Table 9 and FIG. 9.

TABLE 9

The average concentration of bovine somatotropin in milk, ng/ml

| Day | Injected group | Control group |
|---|---|---|
| 5  | 0.3310 | 0.3204 |
| 12 | 0.3184 | 0.3537 |
| 20 | 0.3557 | 0.2677 |
| 28 | 0.3237 | 0.3812 |
| 35 | 0.3098 | 0.3043 |

Example 21

The composition was prepared and tested according to the same procedure as Example 20, except that 5 ml of composition was injected. The increase ratio and the concentration of bovine somatotropin in serum and milk are shown in Table 10, 11, 12 and FIG. 10, 11, 12.

TABLE 10

Cumulative average daily milk production, kg/day

| Day | Injected group | Control group | Increase ratio (%) |
| --- | --- | --- | --- |
| −5–0 | 25.7 | 25.7 | — |
| −7 | 27.5 | 24.4 | 12.2 |
| −14 | 27.9 | 25.0 | 11.4 |
| −21 | 27.1 | 24.9 | 8.5 |
| −28 | 26.6 | 24.5 | 8.9 |

TABLE 11

The average concentration of bovine somatotropin in serum, ng/ml

| Day | Injected group | Control group |
| --- | --- | --- |
| −1 | 15.0 | 10.1 |
| 1 | 79.5 | 17.0 |
| 5 | 38.4 | 12.3 |
| 8 | 40.3 | 9.2 |
| 12 | 24.9 | 14.2 |
| 15 | 18.7 | 13.3 |
| 19 | 14.5 | 8.4 |
| 22 | 20.4 | 11.2 |
| 27 | 17.9 | 15.5 |
| 29 | 21.2 | 14.2 |

TABLE 12

The average concentration of bovine somatotropin in milk, ng/ml

| Day | Injected group | Control group |
| --- | --- | --- |
| 6 | 0.3296 | 0.3043 |
| 16 | 0.3450 | 0.3931 |
| 21 | 0.3700 | 0.4138 |
| 28 | 0.3819 | 0.3483 |

Example 22

Test was carried out using 3 holstein cows in the middle period of the lactation. 7.5 ml of bovine somatotropin compositions including L-α-phosphatidyl choline was injected to them. As a control group, only tocopherol acetate was injected to other 3 holstein cows. For comparison, the daily milk production was measured for 2 weeks before injecting the compositions.

The compositions were injected subcutaneously in the suprascapular region. After the injection, the milk production was measured everyday and the data are shown in Table 13 and FIG. 13.

TABLE 13

The daily milk production before and after the injection, kg/day

| Day | Injected group | Control group |
| --- | --- | --- |
| −14 | 16.6 | 14.9 |
| −13 | 15.8 | 14.9 |

TABLE 13-continued

The daily milk production before and after the injection, kg/day

| Day | Injected group | Control group |
| --- | --- | --- |
| −12 | 14.9 | 11.6 |
| −11 | 16.6 | 15.3 |
| −10 | 15.8 | 13.5 |
| −9 | 15.1 | 12.8 |
| −8 | 14.1 | 12.1 |
| −7 | 14.9 | 13.1 |
| −6 | 15.1 | 14.1 |
| −5 | 14.8 | 13.7 |
| −4 | 14.6 | 13.5 |
| −3 | 14.7 | 13.5 |
| −2 | 15.1 | 13.6 |
| −1 | 13.0 | 13.2 |
| 0 | 15.8 | 12.9 |
| 1 | 18.3 | 13.4 |
| 2 | 18.4 | 14.1 |
| 3 | 17.5 | 14.3 |
| 4 | 19.0 | 13.4 |
| 5 | 20.2 | 14.4 |
| 6 | 19.7 | 14.5 |
| 7 | 18.1 | 13.5 |
| 8 | 19.8 | 14.1 |
| 9 | 17.5 | 14.2 |
| 10 | 19.2 | 15.4 |
| 11 | 19.0 | 16.0 |
| 12 | 20.0 | 17.0 |
| 13 | 18.8 | 15.5 |
| 14 | 17.8 | 15.6 |
| 15 | 17.2 | 15.5 |
| 16 | 18.3 | 16.8 |
| 17 | 17.9 | 16.9 |
| 18 | 16.8 | 14.4 |
| 19 | 17.5 | 16.4 |
| 20 | 16.5 | 14.8 |
| 21 | 15.6 | 15.1 |
| 22 | 16.0 | 15.5 |
| 23 | 16.9 | 15.3 |
| 24 | 16.7 | 15.7 |
| 25 | 17.3 | 16.0 |
| 26 | 16.5 | 15.8 |
| 27 | 15.1 | 15.1 |
| 28 | 17.3 | 16.6 |

Before the injection and the 3rd, 7th, 14th, 21st and 28th days after the injection, the blood sample was collected. blood samples were analyzed for bovine somatotropin by radioimmunoassay. The resukts are shown in Table 14 and FIG. 14.

TABLE 14

The bovine somatotropin concentration in serum, ng/ml

| Day | Injected group | Control group |
| --- | --- | --- |
| 0 | 15.175 | 15.095 |
| 3 | 35.699 | 15.195 |
| 7 | 21.678 | 15.501 |
| 1 | 415.123 | 14.516 |
| 2 | 113.851 | 14.460 |
| 2 | 814.483 | 12.393 |

Example 23

Test was carried out using 15 castrated hogs weighing about 60kg. The porcine somatotropin compositions including L-α-phosphatidyl choline were injected by an amount of 1.2 ml per head to 5 hogs, and by an amount of 1.8 ml per head to other 5 hogs. The other 5 hogs were used as control group without any injection.

Before the injection and everyweek after the injection, their body weights were measured at regular time. The average daily gain (ADG, kg/day) was calculated. The feed efficiency (FE) was calculated as follows;

$$FE* = \frac{\text{The amount of feed intake}}{\text{The amount of increased body weight}}$$

(* Lower FE value represents higher efficiency).

The back fat thickness (FT) was measured and the decrease ratio of FT was calculated. The results are shown in Table 15.

TABLE 15

Average daily weight gain and feed efficiency from the injection of porcine somatotropin

|  | Control group | Injected group 1 | Injected group 2 |
|---|---|---|---|
| 1st week: | | | |
| ADG | 1.00 | 0.97 | 1.03 |
| FE | 3.05 | 3.26 | 2.75 |
| 2nd week: | | | |
| ADG | 0.96 | 0.77 | 0.87 |
| FE | 3.36 | 4.48 | 4.16 |
| 3rd week: | | | |
| ADG | 1.07 | 0.98 | 1.00 |
| FE | 3.14 | 2.95 | 3.45 |
| 4th week: | | | |
| ADG | 0.90 | 1.05 | 1.09 |
| FE | 4.35 | 3.57 | 3.13 |
| 5th week: | | | |
| ADG | 0.84 | 0.81 | 1.04 |
| FE | 5.05 | 4.37 | 3.65 |
| 6th week: | | | |
| ADG | 1.09 | 1.14 | 1.08 |
| FE | 4.91 | 4.04 | 4.30 |
| 1st–6th weeks: | | | |
| ADG | 0.98 | 0.96 | 1.02 |
| FE | 3.65 | 3.50 | 3.46 |
| Increase rate of FE (%) | — | 4.1 | 5.2% |
| 1st–6th weeks: | | | |
| Decrease rate of FT (%) | — | 6% | 9% |

Example 24

The porcine somatotropin compositions prepared as in Example 19 were injected by an amount of 0.9 ml per head every three weeks to 5 hogs, by an amount of 1.8 ml per head every three weeks to other 5 hogs [Injected group 2], and by an amount of 6 mg per head everyday to other 5 hogs (daily injected group). The other 5 hogs were used as control group without any injection. Their body weights were measured every 2 weeks. ADG, FE, the increase rate of FE and the decrease rate of FE were determined as in Example 23 and the results are shown in Table 16.

TABLE 16

Average daily gain and feed efficiency from the injection of porcine somatotropin

|  | Control group | Daily injected group | Injected group 1 | Injected group 2 |
|---|---|---|---|---|
| 1st–2nd weeks: | | | | |
| ADG | 1.01 | 0.85 | 1.06 | 1.02 |
| FE | 2.92 | 2.60 | 2.79 | 2.70 |
| 3rd–4th weeks: | | | | |
| ADG | 0.91 | 1.04 | 1.09 | 1.04 |
| FE | 3.87 | 2.68 | 2.98 | 3.09 |
| 5th–6th weeks: | | | | |
| ADG | 0.88 | 0.98 | 0.64 | 1.01 |
| FE | 3.67 | 3.14 | 5.06 | 3.65 |
| 1st–6th weeks: | | | | |
| ADG | 0.93 | 0.95 | 0.93 | 1.02 |
| FE | 3.45 | 2.79 | 3.37 | 3.16 |
| Increase rate of FE (%) | — | 19.1% | 2.3% | 8.4% |
| 1st–6th weeks: | | | | |
| Decrease rate of FT (%) | — | 39% | 24% | 11% |

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A method of producing a sustained release formulation of a somatotropin which comprises:
   (a) forming an aqueous solution of a lecithin and a somatotropin to form liposomal somatotropin;
   (b) lyophilizing said liposomal somatotropin;
   (c) suspending said lyophilized liposomal somatotropin in an α-tocopheryl acetate to form a mixture wherein said α-tocopheryl acetate is present in an amount of from 90 to 98% by weight based on the total weight of said α-tocopheryl acetate and said lecithin and said lecithin is present in an amount of from 2 to 10% by weight based on the total weight of said α-tocopheryl acetate and said lecithin; and
   (d) homogenizing said mixture to produce said sustained release formulation of somatotropin, wherein said somatotropin is present in an amount of from 1% to 10% by weight of said sustained release formulation.

2. The method according to claim 1, wherein said somatotropin is selected from the group consisting of bovine somatotropin, porcine somatotropin, and ovine somatotropin.

3. The method according to claim 2, wherein said somatotropin is recombinantly prepared bovine somatotropin.

4. The method according to claim 2, wherein said somatotropin is recombinantly prepared porcine somatotropin.

5. The method according to claim 1, wherein said lecithin is extracted from soy bean or egg yolk.

6. The sustained release somatotropin formulation produced according to the method of claim 1.

7. A slow release parenteral composition produced by the process of providing a lyophilized mixture comprising somatotropin and a release delaying agent, suspending said lyophilized mixture in a tocopherol compound to form a suspension wherein said tocopherol compound is selected from the group consisting of tocopherol and tocopheryl acetate, and is present in an amount of from 90 to 98% by weight based on the total weight of said tocopherol compound and said release delaying agent, and said release delaying agent is present in an amount of from 2 to 10% by weight based on the total weight of said tocopherol compound and said release delaying agent, and homogenizing said suspension wherein said somatotropin is present in an amount of from 1% to 10% by weight of said slow release parenteral composition.

8. The composition according to claim 7, wherein said release delaying agent is a choline compound.

9. The composition according to claim 8, wherein said release delaying agent is a choline compound consisting of phosphatidyl choline.

10. The composition according to claim 8, wherein said release delaying agent is a choline compound comprising an extract of egg yolk.

11. The composition according to claim 11, wherein said somatotropin is an animal somatotropin.

12. The composition according to claim 11, wherein said somatotropin is an animal somatotropin selected from the group consisting of bovine somatotropin, and porcine somatotropin.

13. The composition according to claim 12, wherein said animal somatotropin is obtained from a recombinantly prepared microorganism.

14. The composition according to claim 7, wherein said tocopherol compound is present in an amount of from 95 to 98% by weight based on the total weight of said tocopherol compound and said release delaying agent, and said release delaying agent is present in an amount of from 2 to 5% by weight based on the total weight of said tocopherol compound and said release delaying agent.

* * * * *